US00PP21696P3

(12) United States Plant Patent
Benardella

(10) Patent No.: US PP21,696 P3
(45) Date of Patent: Feb. 8, 2011

(54) ROSE PLANT NAMED 'BENSIETE'

(50) Latin Name: *Rosa hybrida*
Varietal Denomination: BENsiete

(75) Inventor: Frank Benardella, Millstone Township, NJ (US)

(73) Assignee: Nor'East Miniature Roses, Arroyo Grande, CA (US)

( * ) Notice: Subject to any disclaimer, the term of this patent is extended or adjusted under 35 U.S.C. 154(b) by 79 days.

(21) Appl. No.: 12/322,830

(22) Filed: Feb. 6, 2009

(65) Prior Publication Data

US 2010/0205701 P1 Aug. 12, 2010

(51) Int. Cl.
*A01H 5/00* (2006.01)

(52) U.S. Cl. ..... Plt./136
(58) Field of Classification Search ..... Plt./136
See application file for complete search history.

(56) References Cited

U.S. PATENT DOCUMENTS

PP11,369 P * 5/2000 Zary ..... Plt./139

* cited by examiner

*Primary Examiner*—Wendy C Haas

(57) ABSTRACT

This new rose plant, 'BENsiete', bears fully double flowers with hybrid tea form, primarily one to a stem. Flowers can last well on the plant, opening and fading slowly, and ten days or more as cut flowers. Fragrance is moderate. The plant is of a medium size and upright growing habit. 'BENsiete' is well suited as a garden perennial, a large container plant and for cut flowers.

1 Drawing Sheet

Genus and species: *Rosa hybrida.*
Varietal denomination: 'BENsiete'.

BACKGROUND OF THE INVENTION

The present invention relates to a new and distinct variety of hardy, bush-type rose plant. This new variety is from a single seedling originated by Frank A. Benardella under controlled conditions in a greenhouse in Millstone Township (formerly, Englishtown), N.J., by crossing the following two rose plants:

The seed parent is a pink miniature rose from this same breeding program, 'Perfection' (not patented).

The pollen parent is a red hybrid tea, 'JACecond', (U.S. Plant Pat. No. 11,369).

This resulting new rose has been given the code name of 'BENsiete' and the trade name of Ambiance.

The primary goal of this breeding program is to produce unique roses with award winning, hybrid tea form on plants having favorable attributes that will increase public appeal. To achieve this goal roses are selected for this hybridizing program primarily for their award winning, hybrid tea form. Pertaining to this particular cross, both parents have been noted for their exhibition form flowers that are often borne one to a stem. Both are traits visible in this new invention.

SUMMARY OF THE INVENTION

The present invention relates to a new and distinct variety of hardy, bush-type rose plant. The most significant feature is the light apricot-pink color of its fully double, hybrid tea form flowers that expand, on average, to 2¾ to 3½ inches. It has several other attributes that further set it apart from all other presently available roses, of which I am aware. They are its unique combination of:

Flowers that open slowly and last a long time on the plant;
Flowers that are borne primarily singly;
Flowers that can last ten days or more as cut flowers;
Moderate fragrance;
Upright plant that generally grows two to three feet tall;
Uniform branching;
Dark-green, matte foliage;
Its broad prickles;
Above average resistance to blackspot;
A plant that grows and blooms very well, both, in a greenhouse, and outdoors as a perennial garden decoration or in large containers.

The new invention and its parents all have hybrid-tea type, exhibition form flowers. It is easily distinguished from its parents.

This new invention, 'BENsiete', has flowers of a soft, apricot-pink. The seed parent in this cross, 'Perfection', has flowers of a solid medium-pink. The flowers of the pollen parent, 'JACecond', are a solid red.

This new invention has flowers that expand to 2¾ to 3½ inches across, on average. The flowers of 'Perfection' are expected to expand 1¾ inches across, on average. Open blooms on 'JACecond' average 4 inches across, 'BENsiete' is larger than its seed parent, 'Perfection', a miniature rose which has a compact bush that matures at 18 to 24 inches high. 'BENsiete' is much slower growing than its pollen parent, 'JACecond', which can grow up to 5 feet tall and 4 feet wide in its first year. 'BENsiete' is not expected to reach more than 18 inches in its first year and 2½ to 3½ feet when mature.

Both 'JACecond' and new invention have flowers borne primarily singly on an upright plant. 'Perfection' has flowers borne in clusters on a compact and bushy miniature bush.

Perhaps the rose from this same breeding program most closely resembling this new invention is 'BENpete' (not patented) with it shares the same pollen parent, 'JACecond'. Visually, it is evident that the flowers of both BENpete and this new invention have hybid tea-type, exhibition form, and that both plants have an upright habit. This new invention and 'BENpete' have the similar open bloom size and petal counts. The most notable differences are:

This new invention has soft, apricot-pink flowers, while 'BENpete' has predominately red flowers with white at the base and on the reverse of the petals.

Both plants have semi-glossy foliage, though the foliage of 'BENpete' is somewhat smaller and a bit darker.

'BENpete' is more apt to have multiple flowers per stem.

Asexual reproduction by cuttings of this new variety in Millstone Township, N.J., and Arroyo Grande, Calif., show that all distinguishing characteristics of this rose continually come true to form.

BRIEF DESCRIPTION OF THE DRAWING

The accompanying illustration shows flowers from plants grown in different locations and at different times of the year.

1. The largest image, image number 1 taken in January of 2009, shows buds and flowers in different stages of development, and some foliage from 2 year old plants grown in a plastic covered greenhouse in Arroyo Grande, Calif.
2. Image number 2, in the upper right hand corner of the enclosed illustration, was also taken in January of 2009. It is of flowers from a seven year old plant grown in a glass-covered greenhouse in Millstone Township, N.J. This image shows one bloom as the petals began to unfurl, and one bloom at half open, exhibition stage.
3. Image number 3 shows a single bloom as grown in a shaded, plastic covered greenhouse in Arroyo Grande, Calif., in November of 2005. This image indicates the fewest petals are from this lower light condition.
4. Image number 4 is flowers and buds from five year old plants grown out doors in the ground in Arroyo Grande, Calif., in January of 2009. (It is unusual for roses to be in flower outdoors in Arroyo Grande in January but the weather had been unseasonably warm the previous three months.)
5. Image number 5, across the bottom of the illustration, shows a stem with some prickles, leaves, and sepals. This is a candelabra stem from the same plants used for image number 4.

Color is as nearly correct as it is possible to make in a color illustration of the character.

BOTANICAL DESCRIPTION OF THE PLANT

Unless otherwise noted, the following observations, measurements, values and comparisons are from a four-year-old plant of *Rosa hybrida,* 'BENsiete', as grown outdoors in Ipswich, Mass. The plant was received in Massachusetts in April of 2008, in a 12-inch plastic nursery container in artificial soil mix. In July of 2008, it was transplanted into a 5-gallon container in a peat moss and compost mix. Observation was continued through October. Phenotypic expression varies with environmental, cultural, and climatic conditions. Color references are made using The Royal Horticultural Society Colour Chart, except where common terms of color are used.

FLOWERS

BLOOMING HABIT: This new invention is a repeat blooming rose bush. Flowering stems were strong, and very slightly crooked, usually at a single node but not consistently at the same node. Flowers were borne mostly singly but also in small clusters of two. New shoots developed from nodes immediately below the bloom, beginning their growth in the spring and early summer as the top bud began to unfurl, and in late summer and early fall after the flower faded. The complete cycle repeated every 5 to 6 weeks.

BUD form was ovoidal with an acute apex and truncated at the base. Diameters were measured from 10/32 to 19/32 inch with lengths from 20/32 to 26/32 inch.

BLOOM size averaged from 2¾ to 3½ inches when fully expanded, but were measured from 2 9/16 to 4 inches, often not symmetrical, having the cross diameters different by ⅛ to ½ inch. Depths were measured from 1⅛ to 2⅛ inches, relative to diameter. When buds began to open they had an urceolate shape. Opening blooms became high centered, developing a convex upper profile and a shallow-crescent to deeply concave lower profile. Blooms opened slowly, taking 6 days or more until the bloom reached exhibition stage at half open, six days to go from exhibition stage to full open, and about another six days to go from full open to fade. Cut flowers can last ten days or more.

PETALS were moderately thick and seemed to become thicker as they aged. Substance was excellent. Outer petal edges recurved slightly. The outer petals were imbricated. Progressing towards the center of the flower the petals became randomly closer together, in some instances one was on top of another, and the upper halves of the petals were curled and twisted around one another.

The UPPER SURFACE of the petals was smooth and satiny; the outer petals became coriaceous as they aged. Primary veins radiated out from the point of attachment. Their recession progressed from ever so slight on the young petals to slight on the older petals.

The REVERSE was satiny and glabrous. The veins were clearly visible, protruding slightly, and usually became a color different from the surrounding petal surface.

The SHAPE of the outer petals was obovate-rotundate. Inner petals were obovoid. The outer margin was crescent-shaped with a notch at the apex. The base of the outer petals was crescent-shaped. The base of the inner petals was broadly obtuse.

PETAL COUNTS varied from 32 to 80 with 4 to 25 petaloids. The lower petal and petaloid counts were noted on the flowers grown in the shaded, plastic covered greenhouse, where light intensity was lowest.

Widths of the outermost petals varied from 1 9/16 to 2 1/16 and lengths varied from 1⅜ to 2 1/16 inches.

Petals did not drop cleanly from the receptacle after fading, remaining withered and attached for several days.

COLOR visible when the sepals first divided was most often Peach, near 29D, but was also observed much lighter on one occasion in mid-July, a Cadmium Orange, near 23D.

During the first few days, the upper surface of all petals was near white, near 159D, surrounded by Peach, near 29D, along the margins and around the basal area, where it blended into a Canary Yellow between 9C and 9D in the basal area. The point of attachment was a bright yellow, between 3B and 6B.

The reverse was an Orient Pink, near 36D, along the margins, which darkened to a Carrot Red, near 29C, progressing down the petal, and blending into the medium yellow-green, near 154A, of the basal area, with veins of a Primrose Yellow near 4C. The point of attachment was also near 4C. The reverse of the inner petals was a bit different, with a smaller basal area and more of the surface being near 36D.

When half blown, colors remained mostly unchanged. The reverse had darkened along the margins to a Salmon, near 27B, which lightened a bit progressing down the petal to near 29D.

When full blown, the upper surfaces of the outer petals were French Rose, near 49D. The basal area had become an Empire Yellow, near 11D, and the two colors blended in the midsection of the petal. The point of attachment was a very light yellow between 11D and 10D. The upper surface of the inner petals was fading from the 49D and more of it was near 11D.

The reverse had become near 36D with a basal area of a light Mimosa Yellow, near 8D. The veins were slightly raised and near white, a color near 158D. The reverse of the inner petals was almost entirely near 36D as the basal area had noticeably decreased in size.

VARIATION IN PETAL COLORS: The colors of the flowers vary with climatic and edaphic conditions. Some of these variations may be seen in the accompanying illustration.

In June in Essex County, Mass., colors were a bit more orange. During the first few days there was additional color along the margins of near 23D, a Cadmium Orange. The entire reverse was a Carrot Red, near 29C. The basal area of the reverse was a Marigold Orange, near 28C, with areas of near 12D, a very light Aureolin, on both sides of the main vein and with occasional streaks at the edge of the basal area. When half blown, the near 23D along the margins on the upper surface had disappeared from the edges of the margins, leaving them near 29D. The basal area had become between 4C and 4D, and the point of attachment had become near 9C. On the reverse, veins appeared dark green, near 141A, with near 154C along the central vein in the basal area. Other colors were pretty much unchanged.

Flowers on plants grown outdoors, in the ground, in Arroyo Grande, Calif., (see image 4 in the accompanying illustration) were lighter and more of a rose pink than flowers grown in the Eastern United States. On the full open blooms, upper surfaces of the petals were lighter than 36D, an Orient Pink and edged with near 36C. The reverse of outer petals was French Rose, near 49D, with a light Neyron Rose, near 55D along the margins. The reverse of intermediate petals was between 49D and 54D, and edged with near 55C. The reverse of the inner petals was darker still, near 55D, with some areas near 49D and near 49C, and all blending together. Basal areas on the upper surfaces were near 11C. Basal areas on the reverse were near 11D, which also went up through the center of the petal, and blended outward into the petal.

Flowers grown in Millstone Township, N.J. are overall darker, with the deepest color, and more of a yellow-orange tone to them. Flowers grown in the glass-covered greenhouse of the inventor are shown in image 2 of the illustration.

Observations of the flowers from the plants grown in Ipswich, Mass., and Arroyo Grande, Calif., indicated the colors of the flowers became lighter and pinker as the intensity of sunlight increased. Petal counts also seemed to increase as a result of stronger sunlight.

PETALOIDS were interspersed between the petals, and towards the center of the bloom; a few seemed intertwined with the stamens. Their color and texture was the same as those petals immediately behind them. The base of some petaloids was often narrower, and sometimes only one-half of a base. Some appeared to be attached by a filament. Many were very misshapen, from half a petal, to distorted, to miniscule. Some were epipetalous, with stamens or part of a stamen attached to some part of the main vein, which was randomly located in the petal. Margins were observed as deeply cleft to lobed, double-lobed, or even triple-lobed; sinuate; erose; or any combination of these. The largest petaloid observed on a full open bloom was 1¾ inches long and wide, having only the base abruptly narrowed. The smallest were less than 1/16 inch by ⅛ inch, and usually mixed in with the stamens.

SEPALS

There were five sepals permanently attached along the outer edge of the receptacle. They extended beyond the tip of the bud by ½ inch before they began to divide.

SHAPE was ovate with acuminate apices and truncated at the base.

APPEARANCE of the outer surface was semi-glossy when young, and became matte when mature. The inside surface had a fine pubescence.

COLOR of the outer surface was a medium yellow-green near 144A and much lighter, near 145A, in the basal area. The inside surface was a muted light green, between 138D and 191B, with a basal area and up through the center being a darker yellow-green, near 146A.

MARGINS were ciliated. The margins of the two outermost sepals also had glands, stipitate glands and fine foliation.

CHARACTERISTICS of the two outer sepals: There were usually two foliar appendages along each margin, with one being shorter than the other. Usually, they were sinuate or lunate, and the largest of these was bowed. Along the margins of these foliar appendages were smaller acicular appendages, glands and stipitate glands, some with long stipes. The size of all appendages decreased toward the base of the sepal.

The apices of these two outer sepals were foliated with one or two subulate appendages along one margin and three or four along the opposite margin. The size of these appendages decreased toward the tip.

CHARACTERISTICS of the one sepal in-between the inner and outer sepals was often a combination of both the inner and outer sepals, dividing down the center, though there were many occasions when both margins were foliated.

SIZE: The width of all sepals varied from 12/23 to 15/32 inch. Lengths of the outer two sepals were measured at 1 6/32 and 1 7/32 inches. The two inner sepals were measured at 1 4/32 and 1 5/32 inches long. Lengths on the one sepal in-between varied from 1 to 1¼ inches.

RECEPTACLE

RECEPTACLES were conical, truncated at both the top and base. The surface was semi-glossy but became matte as it aged. It appeared glabrous. The diameter at its widest part was 25/64 to 14/32 inch. The height was most often about 11/32 inch but was measured up to 15/32 inch. The color was a light Scheele's Green, near 144B. It was often flushed with a Greyed Red near 178A on the sunward side. An aerial view showed the top surface to be ovoid, about 20/32 inch long and 19/32 inch tapering to 17/32 inch wide. A thick covering of tight stands of long, soft hairs was between the stamens and pistils.

REPRODUCTIVE ORGANS

STAMENS, FILAMENTS AND ANTHERS:

They appeared to be attached throughout upper surface of the receptacle, from the outer edge to the alveola at the center of the receptacle.

Approximately 140 to 154 (or more) were arranged regularly around the outer edge of the receptacle. There were additional shorter ones protruding from amongst the tomentum that covered the top surface of the receptacle; at one count there were 27 of these.

Some of the inner ones and some of the outer ones were folded over, even after the flower had faded, giving the appearance of having very short filaments.

FILAMENTS were a light Chartreuse Green, near 1D. Their lengths ranged from 3/16 to 6/16 inch.

ANTHERS were a very light Primrose Yellow, near 4D.

Pollen sacs were Maize Yellow, near 21B.

PISTILS, STYLES AND STIGMAS originate in the alveola at the center of the upper receptacle surface.

Quantity ranged from 140 to 200.

STYLES were very thin. Those in and toward the very center were straight. Those that were closest to the stamens were curved somewhat, apparently from lack of support. Lengths varied from 3/16 to 1/2 inch, with the shorter ones toward and in the center. Within any one flower, lengths usually were not more than 3/16 inch different. Their color was a dark red, between 46A and 53A toward the top and the rest was a white, near 155A.

STIGMAS were a dull Amber Yellow between 18C and 161C.

HIPS were not observed. This new invention does readily self pollinate.

PLANT

PLANT HABIT was upright and uniformly branched. The general height of these plants is 24 to 36 inches, with a width of 30 inches. Under certain growing conditions, the plant may grow a foot taller. (See VARIATIONS REGARDING THE PLANT following the section on PRICKLES.)

MAIN CANES had a diameter of 15/32 to 1/2 inch. The color of these older canes was a medium green between 147B and 195A.

FLOWERING STEMS had a diameter of 3/16 inch at the base tapering to 2/16 at connection to the peduncle. Their length was quite variable, from 6 1/2 to 13 3/8 inches. They tend to be slightly crooked at a node but not consistently at the same node. In the summer it was noted that most flowering stems had 4 to 6 nodes. In the spring there were usually 7 to 9 nodes. At the top of each flowering stem, at the juncture with the peduncle were at least one small stipulate appendage paired with the same or a one to three-leaflet leaf. New growth was near 144B and became between 147B and 137C.

PEDUNCLES were straight and very strong with a semi-glossy surface. Lengths were most often measured about 1 5/16 inches but varied from 1 6/32 to 1 17/32 inches. Diameters were generally 6/32 inch right below the receptacle, tapering to 4/32 inch and then increasing to 5/32 inch at the base. The color was near 144D below the receptacle and became near 144A at the base. They were flushed on the sunward side with near 178B. The surfaces had numerous stipitate glands, decreasing in quantity toward the receptacle. The glands were near 178B.

FOLIAGE

LEAVES were arranged alternately on the stems. They were pinnately compound with five to seven leaflets but also with three. Seven-leaflet leaves were about one inch longer than five-leaflet leaves.

Five-leaflet leaves were measured 3 1/8 to 4 1/2 inches long.

Seven-leaflet leaves were measured 4 to 5 1/16 inches long.

LEAFLETS were ovate. Serration was simple with a gland at the tip of each serrate. The length of terminal leaflets on mature leaves varied from 2 15/32 to 2 23/32 inches. Widths varied from 1 9/16 to 1 13/16 inches.

The upper surface was glabrous and matte to semi-glossy. The main and primary lateral veins are equally recessed.

The undersurface was matte and coreacious. The venation pattern was costate, with the main vein protruding entirely and the primary lateral veins protruding somewhat.

Color on the upper surface of young leaflets was a medium green between 137C and 147B, with the glands along the margins of near 185A. The reverse was a medium green between 143B and 191A, flushed with varying degrees of near 185A.

Color of older foliage was a dark green between 149A and 139A. The reverse was between 137B and 147B. Main veins were lighter, near 144C.

PETIOLE, RACHIS AND PETIOLULES: The coloring and texture of the petiole, rachis and petiolules were the same.

Color on young leaves on the entire adaxial surface was heavily flushed a deep purple-red, between 183A and 178A. The reverse is a medium green between 195A and 146B.

Color on the old foliage on the adaxial surface was a medium Scheele's Green, near 143B, in the groove, with the ridges the same dark green color as the upper leaflet surface. The reverse was a lighter Scheele's Green, near 144B.

On the adaxial surfaces, there were stipitate glands along all ridges; grooves were glabrous with the exception of many stiff hairs at the juncture of the leaflets.

The abaxial surfaces were glabrous with the exception of a single prickle, or two or three prickles along the rachis.

Length of the petioles on the seven-leaflet leaves varied from 5/8 to 7/8 inch. On the five-leaflet leaves it was longer, varying from 23/32 to 1 5/32 inches.

Lengths of the rachis on the seven-leaflet leaves varied from 1 4/16 to 1 15/16 inches. Rachises on the five-leaflet leaves were shorter, varying from 10/16 to 11/16 inch.

The length of the petiolules to terminal leaflets was not affected by the number of leaflets or the overall length of the leaf. They ranged in length from 19/32 to 25/32 inch.

STIPULES were located in even pairs attached to the base of the petiole for about 13/32 inch with an additional 5/32 to 10/32 angled outward at about a 45° angle from the petiole. Margins were somewhat curled under, to the greatest degree at the base, and decreasing to becoming flat at or before the point where the tip begins to angle outward. The margins are lined with gland-tipped serrates with a few stipitate glands on and between some serrates. The color was near 137B.

PRICKLES

PRICKLES can be numerous or 'average' in number. When young, they tapered to a point, angled downward, and curved or hooked downward. On the older canes, they had developed into a broadly deltoid profile, but still slightly angled downward. The shape of the bases was very narrow-oblong. Widths of the bases varied from 3/32 to 4/32 inch, relative to the overall size of the prickle. The bases of medium sized prickles were generally the same as the length as the prickle; the bases of the shorter prickles were shorter than the prickle; and the bases of the longest prickles were usually longer than the prickle.

On main canes, there was one in the first one inch from the base of the cane and five in the first two inches. They were generally 4/32 to 11/32 inch long.

On the primary laterals, there were seven to eight in three inches. Lengths varied from only 1/16 inch long to 3/8 inch long.

On flowering stems there were four to five in three inches and nine to eighteen in five inches. Lengths varied from 2/16 to 5/16 inch.

When young, the base of the prickle was near 182A, a medium shade from the Greyed-Red Group, and a darker Greyed-Purple, near 183A toward and at the tip. Those prickles exposed to more sun were entirely near 183A, but only on the side receiving the most sun. As they aged, the color lightened to near 165C from the Greyed-Orange Group. When old, the prickles had become a lighter beige-color, between 165D and 199D.

VARIATIONS REGARDING THE PLANT: A difference in day and night temperatures greater than around 30° F. can cause the plant to send up long, very fast growing canes. These may originate from below the ground, at or near the base of the plant. They are often referred to as candelabras because of the large number of blooms originating near the top of a usually long cane. On this new invention, they terminated in a large spray of flowers. The color of these canes was the same as new growth, and gradually became the same color as the older wood on the plant. The quantity of prickles was much greater on these canes, with more than 20 in each of the first two inches from the base. The largest leaves were found on these candelabras.

RESISTANCE to blackspot was better than average. The plant has only average resistance to powdery mildew. Downy mildew and rust were not observed.

HARDINESS was tested in zones 5 through 10. While the plant was not killed by the cold nor bothered by the heat, it did not survive a spring of freezing and thawing.

The invention claimed is:

1. A new and distinct variety of rose plant is claimed, substantially as described and illustrated herein.

* * * * *

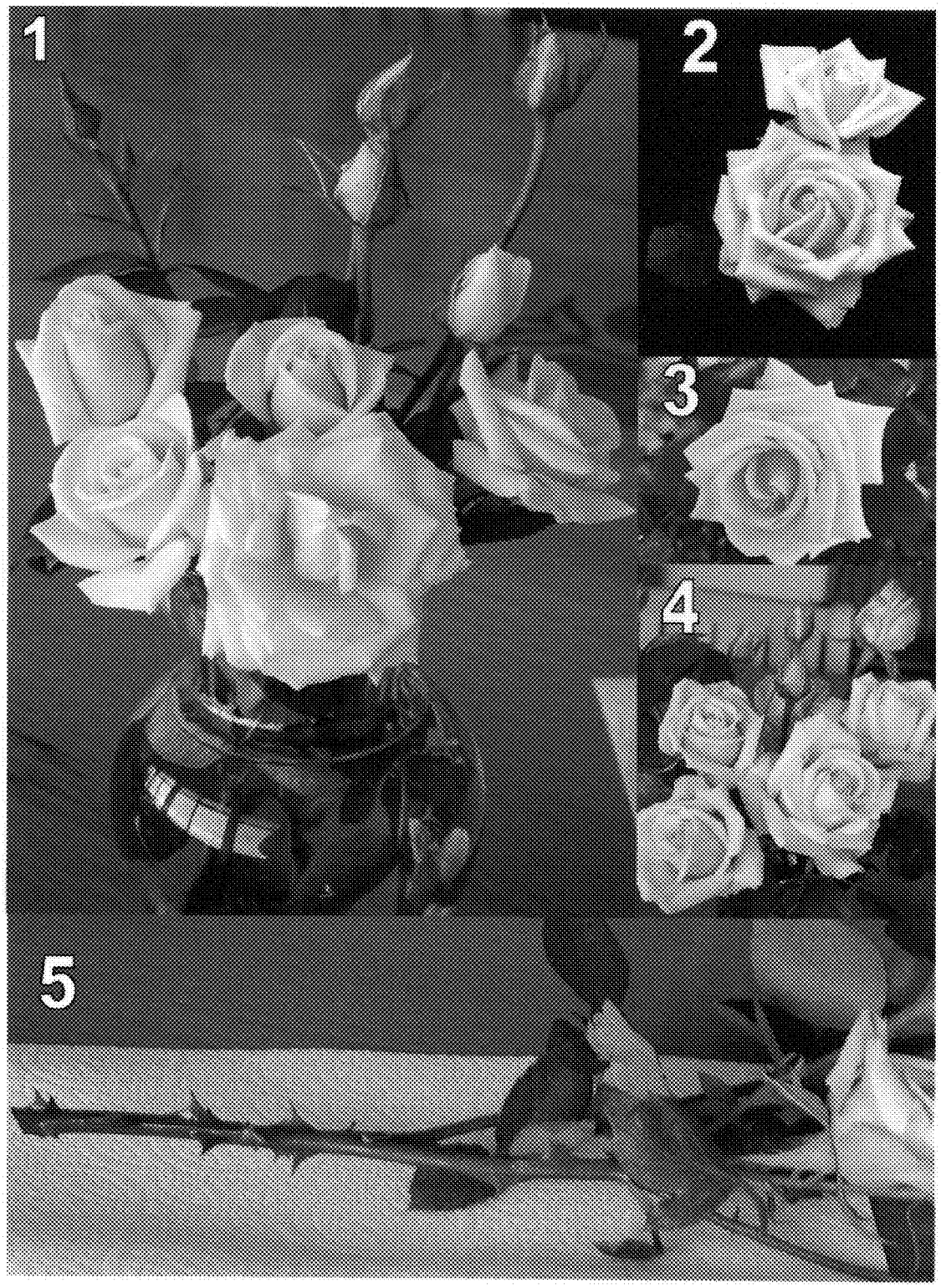
1
2
3
4
5